United States Patent
Siepser

[11] Patent Number: 5,098,438
[45] Date of Patent: Mar. 24, 1992

[54] PROCEDURES FOR INTRAOCULAR SURGERY

[76] Inventor: Steven B. Siepser, 866 Downingtown Pike, West Chester, Pa. 19380

[21] Appl. No.: 571,745

[22] Filed: Aug. 23, 1990

[51] Int. Cl.⁵ ............................................. A61F 9/00
[52] U.S. Cl. .................................. 606/107; 606/161; 606/166; 623/4; 623/5; 623/6
[58] Field of Search ..................... 606/107, 161, 166; 623/4, 5, 6

[56] References Cited

U.S. PATENT DOCUMENTS

| | | | |
|---|---|---|---|
| 2,710,448 | 6/1955 | Andrews | 30/162 |
| 3,256,874 | 6/1966 | DeMarco | 606/170 |
| 3,882,872 | 5/1975 | Douvas et al. | 128/305 |
| 3,945,117 | 3/1976 | Beaver | 606/172 |
| 3,967,377 | 7/1976 | Wells | 606/170 |
| 4,127,903 | 12/1978 | Schachar | 3/13 |
| 4,180,075 | 12/1979 | Marinoff | 128/305 |
| 4,324,044 | 4/1982 | Shahinian | 606/172 |
| 4,688,570 | 8/1987 | Kramer et al. | 606/172 |
| 4,750,498 | 6/1988 | Graham | 606/107 |
| 4,790,845 | 12/1988 | Grendahl et al. | 623/6 |
| 4,888,015 | 12/1989 | Domino | 606/107 |
| 4,908,015 | 9/1990 | Anis | 604/22 |
| 5,026,393 | 6/1991 | Mackool | 606/107 |

FOREIGN PATENT DOCUMENTS 0448013 10/1974 U.S.S.R.
1533669 12/1989 U.S.S.R.

OTHER PUBLICATIONS

Brochure, The Surgical Armamentarium, Instruments Professional Equipment, American V. Mueller (1980).
Emery, Jared M., and McIntyre, David J., "Incision", *Extracapsular Cataract Surgery*, Ch. 24, pp. 135-145, The C.V. Mosby Company (St. Louis 1983).

*Primary Examiner*—Stephen C. Pellegrino
*Assistant Examiner*—Glenn K. Dawson
*Attorney, Agent, or Firm*—Woodcock Washburn Kurtz Mackiewicz & Norris

[57] ABSTRACT

A novel method for performing intraocular surgery is described in which a radial incision is first made in the sclera of the eye, a subsurface scleral pocket lateral and anterior to the radial incision is then created, the subsurface scleral pocket extending anteriorly to the cornea of the eye, and finally a transverse incision is made from the pocket through the cornea into the anterior chamber of the eye. Through these incisions a damaged lens can be efficiently and effectively removed and replaced with a new lens. Various post-operative benefits are observed as a result of employing this procedure.

21 Claims, 3 Drawing Sheets

PROCEDURES FOR INTRAOCULAR SURGERY

BACKGROUND OF THE INVENTION

The present invention relates to the field of ophthalmic surgery, and more particularly to intraocular surgery, and finds special importance in the treatment of lens disorders, such as cataracts, which treatment utilizes phacoemulsification and artifical lens implantation techniques.

Vision, in vertebrate systems, is dependent upon the eye forming an image of an object and sending that image to the sensory centers of the brain. In this process, light rays from an object pass through the cornea, the aqueous humor, the pupil, the intraocular lens and the vitreous humor of the eye. These rays finally reach the retina where they stimulate the optic nerve cells. In turn, the optic nerve carries messages from the nerve cells to the visual cortex of the brain. In essence, the disc-shaped intraocular lens of the eye performs the same function as the lens of a camera, being responsible for focusing incoming light rays onto the retina, the image registering portion of the eye.

The lens of the eye is subject to damage by physical or other external trauma, whether accidental or otherwise, and also by the formation of cataracts. Such damage can affect the ability of the lens to perform its function of focusing and transmitting light rays.

The formation of cataracts are a common disorder of the eye, and are one of the leading causes of blindness in the United States. A cataract is a physical change in the lens characterized by a transformation of the normally transparent lens to a cloudy or opaque state. As a consequence, adequate light cannot reach the associated retina, and vision becomes increasingly blurred. There are several basic types of cataracts, including congenital cataracts, cataracts caused by accidental injury, cataracts caused by disease such as diabetes or glaucoma, and so-called senile cataracts which commonly appear in persons over about 65 or 70 years of age.

Cataracts and other deficiencies of the lenses are generally treated by surgical procedures in which the damaged lens is removed. While removal of the clouded lens will restore light perception, full rehabilitation requires that the refractive power of the natural lens be supplied through some other means.

In the past, the biological lens was simply replaced by glasses and/or contact lenses. However, there were a number of disadvantages and limitations associated with these rehabilitative measures. For example, the magnitude of the optical compensation required to replace a natural lens necessitated very strong lenses, resulting in glasses which were both clumsy and heavy, or contact lenses which were frequently incapable of providing the high focusing strength needed. Moreover, spectacles produced major optical distortions, and some patients, particularly older patients, have found it difficult to adjust to the wear and maintenance of contact lenses.

However, in recent years, advances have led to the development of artificial lenses that are able to replace the damaged natural lens. The availability of artificial intraocular lens implants serves to eliminate or at least minimize the need for contact lenses and eyeglasses following surgery. The artificial lenses can be permanently implanted and serve to mimic the function of the original, natural lens. They are convenient, comfortable and are capable of providing the desired optic strength without distortion.

A number of procedures for removing the damaged lens and replacing it with an artificial lens are known. The most frequently employed and favorably regarded methodology is the extracapsular technique wherein a transverse incision is made in the limbus zone directly through the cornea into the anterior chamber. An artificial replacement lens is then carefully inserted into the eye through the same corneal aperture and manipulated by the surgeon into the position previously occupied by the removed natural lens. One of the major advantages of this technique is that a small incision of only about 3 mm is required to remove the natural lens from the eye and insert an artificial lens. There are, however, a number of significant disadvantages associated with the use of this procedure. Specifically, the transverse incision requires the use of a number of sutures, resulting in additional discomfort and irritation during the healing process. Moreover, a significant amount of undesirable drag on the incisional edges during instrument insertion has been evident. Furthermore, induced astigmatism has been observed in patients treated using this procedure.

New and/or better surgical procedures are needed. The present invention is directed to this important end.

Specifically, it is an object of the present invention to provide a surgical procedure that minimizes trauma to the patient's eye during surgery. A further object is to provide a surgical process that affords the patient a relatively comfortable convalescence following eye surgery. An additional object of the invention is to provide an opthamological technique that minimizes the potential for induced astigmatism. An even further object of the invention is to provide a surgical methodology for the eye that requires less incisional sutures. A still further object is to provide procedure for eye surgery which employs an incision of a sufficient size to enable the use of phacoemulsification techniques and the introduction of an intraocular implant. It is a further object of the invention to provide a surgical process for the eye that results in an incision that experiences minimal drag on its edges during the course of the surgery.

SUMMARY OF THE INVENTION

The foregoing objects of the invention are achieved by the present process. Specifically, the present process is directed to a novel method for performing intraocular surgery wherein (i) a radial incision is first made in the sclera of the eye to a depth of less than the thickness of the sclera, (ii) a subsurface scleral pocket lateral and inferior to the radial incision is then created, the subsurface scleral pocket extending inferiorly a distance to about the cornea of the eye, and finally (iii) a transverse incision is made from the pocket through the cornea into the anterior chamber of the eye. The method may further comprise, if desired, the steps of (iv) removing the natural lens of the eye, and (v) inserting an artificial lens in the eye in the position previously occupied by the natural lens.

The foregoing and other objects and features of the present invention will become better understood through a consideration of the description herein taken in conjunction with the following drawings.

DESCRIPTION OF THE PREFERRED EMBODIMENT OF THE INVENTION

Figure 1:
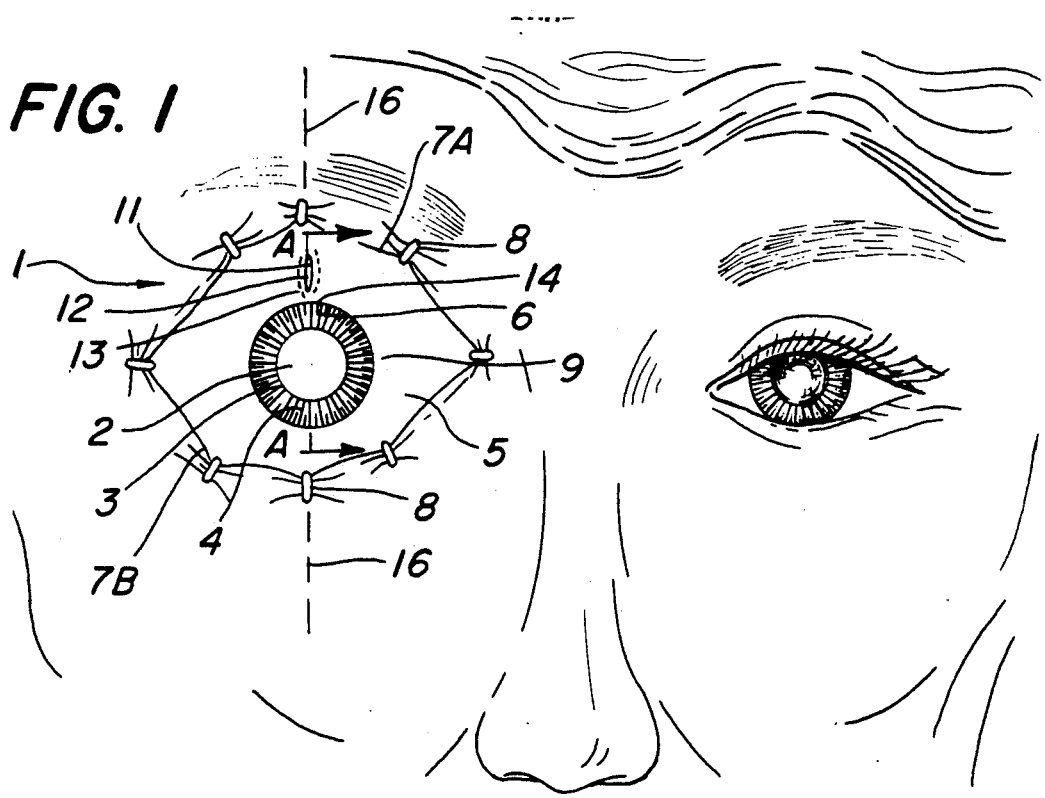
FIG. 1 is a front elevational view of a human eye with the eyelids in a retracted position, showing the novel radial and transverse incisions of the surgical procedures of the present invention.
Figure 2:
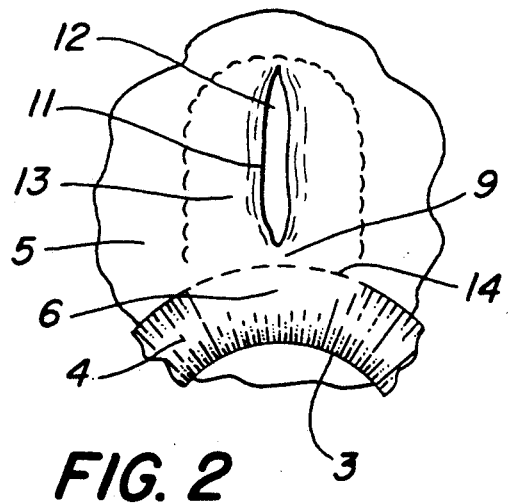
FIG. 2 is an enlargement of a portion of the eye depicted in FIG. 1 showing in greater detail the novel radial and transverse incisions of the present procedures.
Figure 3:
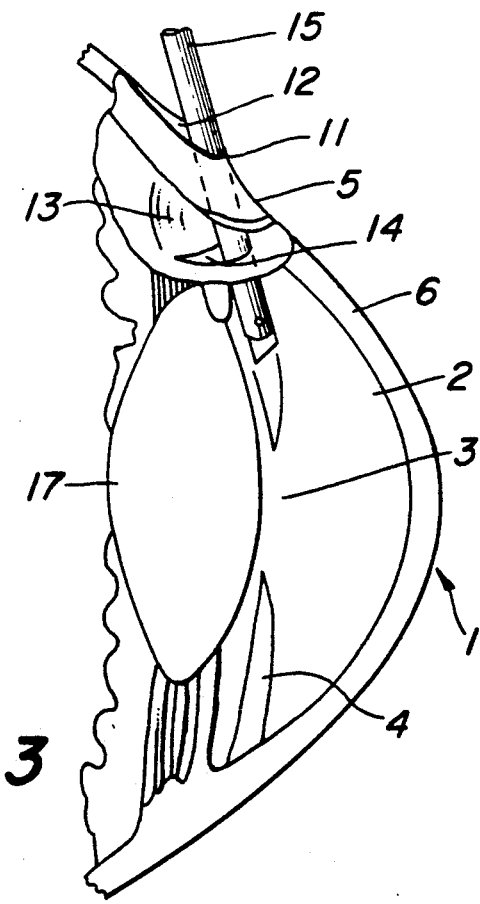
FIG. 3 is a sectional view of the eye depicted in FIG. 1, taken along lines A—A of that figure, showing the novel radial and transverse incisions of the present procedures.

FIG. 1 depicts a human eye 1 with an anterior chamber 2 exposed through a pupil 3 of an overlying iris 4, with a sclera 5 circumferentially surrounding iris 4. A transparent cornea 6 overlies the anterior chamber 2, pupil 3 and iris 4. FIG. 2 shows a sectional view of human eye 1 with cornea 6 overlying anterior chamber 2, pupil 3 and iris 4. Eyelids 7A (upper eyelid) and 7B (lower eyelid), shown in FIG. 1, are in a retracted position, being held in place by sutures 8. Also depicted in each of FIGS. 1 through 3 is a radial incision 11 made in the sclera 5, approximately 1.0 mm from the limbus zone 9, the region of the eye where the sclera 5 and iris 4 meet. By the phrase radial incision it is meant an incision which is radial to the iris 4, as, for example, is radial incision 11 in FIGS. 1 through 3. A radial incision 11 of between about 2.5 mm and 4.0 mm in cord length is generally sufficient for the procedure of the invention.

In accordance with the procedure of the invention, a radial incision 11 is made in sclera 5 of eye 1, using standard instrumentation such as a Grieshaber paufique knife (not shown), to form a scleral orifice 12 less than the thickness of the sclera 5, such that penetration into the anterior chamber of the eye does not occur. Preferably the orifice has a depth of about two-thirds of the thickness of sclera 5. A subsurface scleral pocket 13, as best depicted in FIGS. 1 and 2, is then created lateral to incision 11 (that is, in the scleral regions on both sides of incision 11) as well as inferior to incision 11 (that is, in the scleral region adjacent to the end of incision 11 closest to the iris) using appropriate instrumentation, such as a paufique knife, which is employed through scleral orifice 12 formed by radial incision 11. The subsurface scleral pocket 13 is preferably about 4.0 mm in diameter and extends up to about the cornea 6. A subsurface transverse incision 14, shown in FIGS. 1 through 3, is then made from the subsurface pocket through the cornea 6 into the anterior chamber 2, using a keratome or the like. By the phrase transverse incision it is meant an incision made along a line substantially perpendicular to the radial incision at the inferior most region of the subsurface scleral pocket 13 (that is, the region closest to the iris). Preferably, the subsurface transverse incision 14 is slitlike, having a cord length between about 3.0 mm and about 5.0 mm. The eye 1, as shown in FIG. 1, is as it would be viewed by a surgeon while standing over the patient's head while the patient is in the supine position on an operating table. Preferably, radial incision 11 is located as shown in FIGS. 1 through 3, that is, superior to the iris 4 (i.e., above iris 4, in other words in a position closer to the patient's upper eyelid 7A than lower eyelid 7B) and located along the medial plane 16 of the eye 1 (i.e., the midline plane that divides eye 1 into equal left and right halves).

Capsulotomy and removal of lens 17, shown in FIG. 3, can then be carried out by way of standard techniques using instruments, such as instrument 15, placed into anterior chamber through radial incision 11 and transverse incision 14. Preferably, capsulotomy and lens removal is effected by use of the conventional two-handed in situ phacoemulsification technique. The use of an endocapsular controller is preferred. An artificial intraocular lens, such as standard types, can then be introduced into chamber 2 through incisions 11 and 14 using conventional means. Once the new lens is in place, eye 1 may be left to heal. If desired, one or more sutures, such as those of the mattress type, may be employed to close radial incision 11 and/or transverse incision 14. Advantageously, however, the location and orientation of incisions 11 and 14 are such that sutures are not required for the incisions in order to prevent the egress of aqueous humor. The positive pressure of the eye serves to keep incision 14 closed after surgery is completed, and thus no incisional sutures are needed. Incision 11 also requires no incisional sutures, however, the use of one such incisional suture may be desirable.

Although various conventional surgical instruments, such as knives and blades, may be used when carrying out the surgical procedures described and claimed herein, it has been found that the knives and blades described in my copending patent application, entitled "Surgical Knives For Use In Ophthalmic Surgery", U.S. Ser. No. 572,173, filed concurrently herewith on Aug. 23, 1990, the disclosures of which are hereby incorporated herein by reference in its entirety, are particularly adapted for use with the present procedures. FIGS. 4 through 9, and the text which follows relate to that application.

Figure 4:
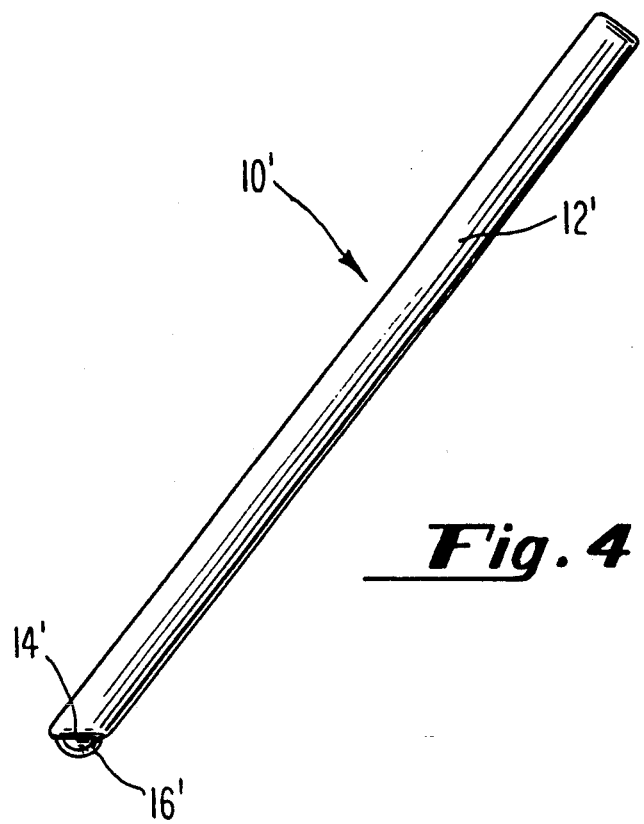
FIG. 4 is a side view of a guarded sclerotomy knife which may be employed in carrying out the present procedures.
Figure 5:
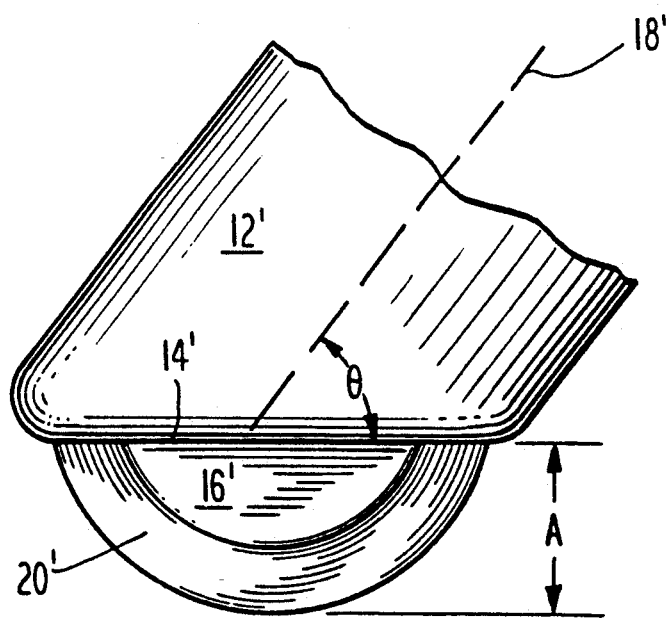
FIG. 5 is an enlarged view of the blade portion of the knife depicted in FIG. 4.

A surgical knife for use in ophthalmic surgery is shown in FIG. 4 and generally designated 10'. Knife 10' is seen to include a handle 12' having a surface 14' formed at on end. A blade 16' is attached to handle 12' by any suitable means and extends a distance outwardly from surface 14'. FIG. 5 is an enlarged view and more clearly shows the relationship of surface 14' and blade 16'.

As shown in FIG. 5, blade 16' extends a distance "A" from surface 14', which distance is less than the thickness of the sclera of the eye. When knife 12' is moved across the eye and blade 16' is pressed against the sclera, a partial incision will result. As knife 10' is pressed against the sclera, blade 16' will penetrate until surface 14' contacts the sclera outer surface. As knife 10' is moved across the sclera and incision of uniform depth is assured so long as surface 14' is kept in contact with the outer surface of the sclera. Such an incision has a depth less than the scleral thickness such that penetration into the anterior or posterior chambers does not occur.

As shown in FIG. 5, handle 12' defines a central axis 18'. Surface 14', which is substantially planar, is formed at an angle $\theta$ to axis 18'. In the preferred embodiment, angle $\theta$ is the range from about 30° to about 60°. It will also be appreciated from FIG. 5, that blade 16' comprises a tip 20', which tip is arcuate shaped. In the preferred embodiment, distance "A", i.e. the distance blade 16' extends from surface 14' is approximately 3 mm. Although distance "A" can be any distance less than the scleral thickness, it is preferred that distance "A" be approximately equal one half scleral thickness.

Figure 6:
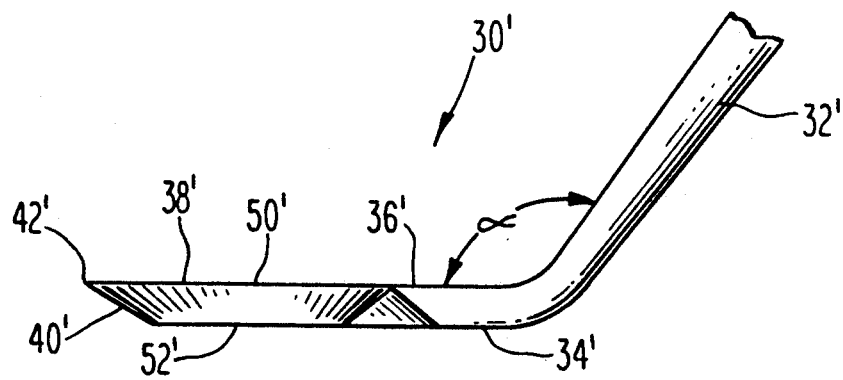
FIG. 6 is a side view of a paufique blade which may be employed in carrying out the present procedures.
Figure 7:
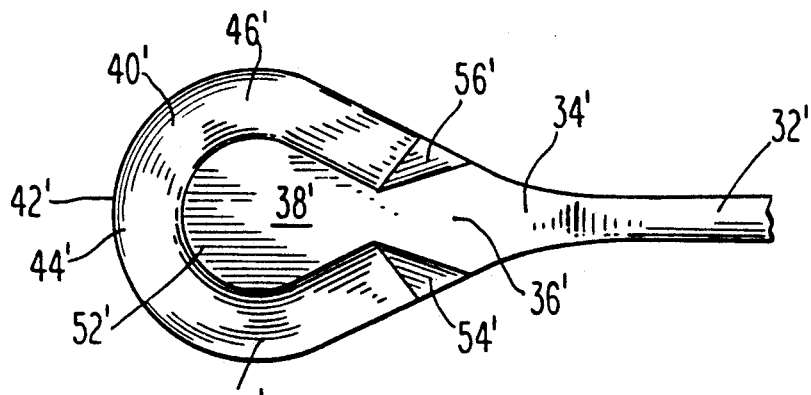
FIG. 7 is a top view of the blade depicted in FIG. 6.

Referring now to FIGS. 6 and 7, a surgical blade for use in ophthalmic surgery is shown and generally designated 30'. Blade 30' is shown to include a first shaft 32' and a second shaft 34'. Shaft 34' is connected to shaft 32' at a predetermined angle α. The preferred embodiment, α is in the range from about 30° to about 60°. Shaft 34' extends a distance from shaft 32' forming a distal end 36'. A tip 38' is connected to the distal end 36' of shaft 34'.

Tip 38' is shown to have a tapered surface 40' extending inwardly and forming a continuous cutting edge 42' on tip 38'. Cutting edge 42' is shown to include a front portion 44' formed at the distal end of tip 38' and two side portions 46' and 48'. It is noted that if an incision is made utilizing knife 10', shown in FIGS. 5 and 6, and further if blade 30' is placed within that incision, rotation and transverse movement of shaft 32' will result in the formation of a subsurface scleral pocket. Utilization blade 30', a pocket can be simply formed on either side of the incision without modifying the incision in any way. Shaft 34' facilitates the formation of such pocket in that it permits tip 38' to have a significantly reduced size. In other words, shaft 34' facilitates the movement of tip 38' within the sclera without a need for modification of the original incision.

As particularly shown in FIG. 7, the cutting edge associated with front portion 44' and side portions 46' and 48' is arc shaped and preferably form a generally circular shape along with outer periphery of tip 38'. A tapered surface 40' extends radially inwardly from such generally circular outer periphery. As shown in FIG. 6, tip 38' includes top surface 50' and bottom surface 52'. Tapered surface 40' extends from cutting edge 42' towards bottom surface 52'. As shown in FIG. 7, tip 38' further includes beveled portions 54' and 56' formed at the connection of tip 38' and shaft 34'. It will also be appreciated from FIG. 7, that shaft 34' extends outwardly so that its sides are substantially continuous with cutting edge 42'. The sides of shaft 34' are rounded. By rounding the sides of shaft 34', it is assured that cutting will only occur in relation to cutting edge 42'.

In the preferred embodiment shaft 34' is approximately 3 mm long from the point of connection to shaft 32' to distal end 36'. It is also preferred that the distance between the cutting edge on side portion 46' to the cutting edge formed on side portion 48', i.e. the diameter of the generally circular tip, be approximately 2 mm. It is still further preferred that the end of shaft 32' be approximately 0.3 mm wide at the point of connection to shaft 34'.

Figure 8:
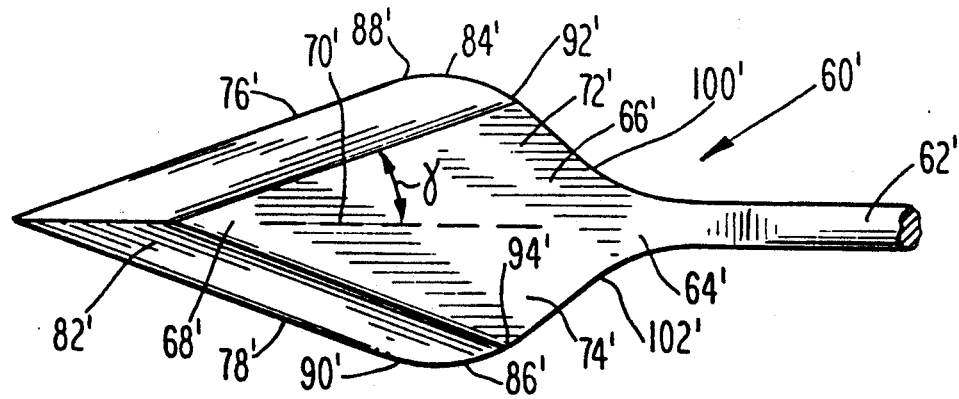
FIG. 8 is a top view of a micro-keratome blade which may be employed in carrying out the present procedures.
Figure 9:
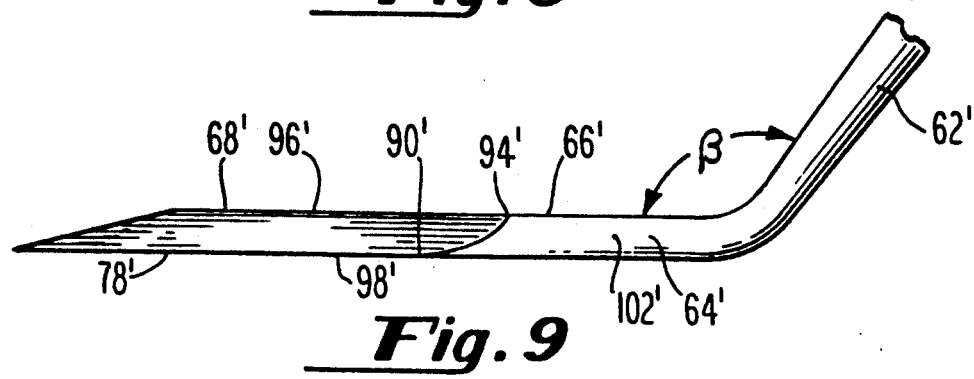
FIG. 9 is a side view of the blade depicted in FIG. 8.

Referring now FIGS. 8 and 9, a surgical blade for use in ophthalmic surgery is depicted and generally designated 60'. Blade 60' is shown to include shaft 62' which is connected to shaft 64'. Shaft 64' extends the distance from first shaft 62' thereby forming a distal end 66'. A tip 68' is connected to distal end 66' of shaft 64'. Tip 68' is shown to extend along a central axis 70'.

Tip 68' is also shown in FIG. 8 as including side portions 72' and 74' which are substantially symmetrical about central axis 70'. Each of side portions 72' and 74' are shown to include a cutting edge 76' and 78', which cutting edges are oriented at an angle γ with respect to central axis 70'. Side portions 72' and 74' are also shown to include a tapered surface 80' and 82', respectively, which tapered surfaces extend away from cutting edges 76' and 78'. Side portions 72' and 74' are further shown to include side edges 84' and 86', which side edges are generally rounded.

As will be appreciated by referring to both FIGS. 8 and 9, cutting edges 76' and 78' extend to the leading ends 88' and 90', respectively. It will also be seen that that portion of the tapered surfaces which is farthest from cutting edges 76' and 78' extends to the trailing ends 92' and 94' of side edges 84' and 86', respectively.

As will be appreciated from FIG. 9, tip 68' includes top surface 96' and bottom surface 98', wherein tapered surfaces 76' and 78' extend towards bottom surface 98'. In other words, cutting edges 76' and 78' are formed on bottom surface 98'. It will also be appreciated from FIGS. 8 and 9, that side portions 72' and 74' include back edges 100' and 102', which back edges are rounded such that if blade 60' is retracted from an incision along a path parallel to central axis 70', back edges 100' and 102' will not modify the incision, i.e. enlarge the incision or cause superficial cuts.

As shown in FIG. 9, shaft 64' and 62' are attached such that an angle β exists therebetween. It is preferred that β lie in the range from about 30° to about 60°. It is further preferred that the length of shaft 64' be approximately 3 mm. It is also preferred that the distance from side edge 84' to side edge 86' be approximately equal to 2 mm. It is still further preferred that shaft 62' be approximately 0.3 mm wide at the point of connection to shaft 64'.

The foregoing tools are particularly adapted to be used together in the surgical procedures of the present invention to produce sutureless openings in an eye for performing surgery therethrough. The micro-sclerotone blade 30' may be advantageously utilized in that rotation and transverse movement of shaft 32' in relation to a radial incision 11 in eye 1 will result in a subsurface scleral pocket 13. Micro-keratome blade 60' is adapted for insertion in the subsurface scleral pocket 13 formed by micro-sclerotone blade 30'. Upon insertion in the subsurface scleral pocket 13, micro-keratome blade 60' is operative for making subsurface transverse incision 14. As will be appreciated from the above, if the micro-keratome blade 60' is removed along a line parallel to the incision, modifiction of the incision, i.e. superficial cuts, should not occur. A guarded sclerotomy knife 10' may be advantageously used for forming the radial incision 11. As described above, such incision has a depth which is less than the scleral thickness such that penetration into the anterior chamber of the eye does not occur. Such radial incision may be utilized in relation to micro-sclerotone blade 30' for the formation of the described subsurface scleral pockets 13. Utilization of the foregoing surgical instruments will provide excellant results when employed in connection with the present intraocular surgical procedures.

The surgical procedures of the present invention are further described in the appended claims. As will be apparent to those skilled in the art, various modifications in the present invention may be made without departing from the spirit and scope of these claims.

What is claimed is:

1. A method for performing intraocular surgery comprising the steps of:

(a) making a radial incision into the sclera of an eye at a depth of less than the thickness of the sclera;
(b) creating a subsurface scleral pocket lateral and inferior to said radial incision, said pocket extending inferiorly a distance to about the cornea of said eye;
(c) making a subsurface transverse incision through said cornea into the anterior chamber of said eye from said pocket; and
(d) performing a surgical procedure in said eye.

2. The method of claim 1 wherein said surgical procedure in step (d) comprises the step of
removing the natural lens of said eye.

3. The method of claim 2 wherein said surgical procedure in step (d) further comprises the step of
inserting an artificial lens in said eye in the position previously occupied by the natural lens.

4. The method of claim 1 wherein said sub-surface scleral pocket is about 4.0 mm in diameter.

5. The method of claim 1 wherein said radial incision is located superior to the iris and along the medial plane of said eye.

6. The method of claim 1 wherein said intraocular surgery is carried out without incisional sutures.

7. The method of claim 2 wherein said sub-surface scleral pocket is about 4.0 mm in diameter.

8. The method of claim 2 wherein said radial incision is located superior to the iris and along the medial plane of said eye.

9. The method of claim 2 wherein said intraocular surgery is carried out without incisional sutures.

10. The method of claim 3 wherein said sub-surface scleral pocket is about 4.0 mm in diameter.

11. The method of claim 3 wherein said radial incision is located superior to the iris and along the medial plane of said eye.

12. The method of claim 3 wherein said intraocular surgery is carried out without incisional sutures.

13. The method of claim 1 wherein said subsurface transverse incision is between about 3.0 mm and about 5.0 mm in cord length.

14. The method of claim 1 wherein said radial incision forms a scleral orifice having a depth of about two-thirds of the thickness of said sclera.

15. The method of claim 1 wherein said radial incision is between about 2.5 mm and about 4.0 mm in cord length.

16. The method of claim 2 wherein said subsurface transverse incision is between about 3.0 mm and about 5.0 mm in cord length.

17. The method of claim 2 wherein said radial incision forms a scleral orifice having a depth of about tow-thirds of the thickness of said sclera.

18. The method of claim 2 wherein said radial incision is between about 2.5 mm and about 4.0 mm in cord length.

19. The method of claim 3 wherein said subsurface transverse incision is between about 3.0 mm and about 5.0 mm in cord length.

20. The method of claim 3 wherein said radial incision forms a scleral orifice having a depth of about two-thirds of the thickness of said sclera.

21. The method of claim 3 wherein said radial incision is between about 2.5 mm and about 4.0 mm in cord length.

* * * * *

UNITED STATES PATENT AND TRADEMARK OFFICE
CERTIFICATE OF CORRECTION

PATENT NO.  : 5,098,438
DATED       : March 24, 1992
INVENTOR(S) : Steven B. Siepser It is certified that error appears in the above-identified patent and that said Letters Patent is hereby corrected as shown below:

Col. 4, line 14    after the word "chamber" insert "2"

Col. 4, line 48    "on" should read "one"

Col. 8, line 19    "tow-" should read "two-"

Signed and Sealed this

Twenty-ninth Day of June, 1993

Attest:

MICHAEL K. KIRK

Attesting Officer      Acting Commissioner of Patents and Trademarks